United States Patent [19]

Miller et al.

[11] 4,067,878

[45] * Jan. 10, 1978

[54] STABILIZATION OF SOLUTIONS OF 3-ISOTHIAZOLONES

[75] Inventors: George A. Miller, Glenside; Ernest D. Weiler, Ambler, both of Pa.

[73] Assignee: Rohm and Haas Company, Philadelphia, Pa.

[*] Notice: The portion of the term of this patent subsequent to Mar. 11, 1992, has been disclaimed.

[21] Appl. No.: 664,137

[22] Filed: Mar. 5, 1976

[51] Int. Cl.$^2$ .......................... C07F 3/04; C07F 3/02; A01N 9/12

[52] U.S. Cl. .............................. 260/302 A; 260/299; 424/245; 424/270

[58] Field of Search .................. 260/299, 302 A, 304; 424/245, 270

[56] References Cited

U.S. PATENT DOCUMENTS 3,870,795   3/1975   Miller et al. .................. 424/270

FOREIGN PATENT DOCUMENTS 2,216,108   11/1972   Germany.

*Primary Examiner*—Nicholas S. Rizzo
*Assistant Examiner*—Diana G. Rivers

[57] ABSTRACT

Solutions of 3-isothiazolones are stabilized against chemical decomposition of the isothiazolone by adding thereto a metal nitrate or a metal nitrite.

16 Claims, No Drawings

STABILIZATION OF SOLUTIONS OF 3-ISOTHIAZOLONES

CROSS-REFERENCE TO RELATED APPLICATION

This application is related to U.S. application Ser. No. 336,659 filed on Feb. 28, 1973, now U.S. Pat. No. 3,870,795.

This invention relates to a method of stabilizing solutions of 3-isothiazolones and to solutions stabilized thereby.

Many 3-isothiazolones, especially those disclosed in United States patent applications Ser. No. 836,660, filed on June 25, 1969, by Sheldon N. Lewis et al., now U.S. Pat. No. 3,761,488, granted Sept. 25, 1973, Ser. No. 855,046, filed on Sept. 3, 1969, by Sheldon N. Lewis et al., now abandoned, and Ser. No. 142,755, filed on May 12, 1971, by George A. Miller et al., U.S. Pat. No. 3,517,022, of George A. Miller et al., granted June 23, 1970, and U.S. Pat. No. 3,544,580, of Sheldon N. Lewis et al., granted Dec. 1, 1970, have been found to possess excellent biocidal properties and to be extremely useful as broad spectrum microbicides. In various types of applications, it is frequently necessary or convenient to formulate the 3-isothiazolones in solution, especially using water or polar organic solvents, such as alcohols, as solvents. While such formulation has no effect on the stability or function of the 3-isothiazolones if used relatively quickly, extended storage of the formulated solutions, especially at elevated temperatures, may result in chemical decomposition of the 3-isothiazolone active ingredient and, thus, lead to reduced biocidal effectiveness of the solution.

It has now been found that a solution of a 3-isothiazolone or of a mixture of 3-isothiazolones can be stabilized against chemical decomposition of the isothiazolone by the addition to the solution of the metal nitrate or a metal nitrite. In a preferred embodiment of the invention, the 3-isothiazolone will be either a compound of the formula

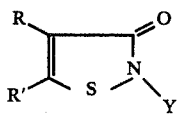 (I)

wherein
Y is a hydrogen atom, an alkyl group of 1 to 18 carbon atoms, an alkenyl or alkynyl group of 2 to 18 carbon atoms, and preferably 2 to 4 carbon atoms, a cycloalkyl group of 3 to 12 carbon atoms, preferably having a 3 to 8 carbon ring, an aralkyl group of up to 10 carbon atoms, or an aryl group of up to 10 carbon atoms;
R is a hydrogen atom, a halogen atom, or an alkyl group, preferably having 1 to 4 carbon atoms;
R' is a hydrogen atom, a halogen atom, or an alkyl group, preferably having 1 to 4 carbon atoms; or
R and R' can be taken together to complete a benzene ring, optionally substituted with one or more halogen atoms, nitro groups, ($C_1$-$C_4$)alkyl groups, cyano groups, ($C_1$-$C_4$)alkoxy groups, or the like;
or a metal salt complex of the formula

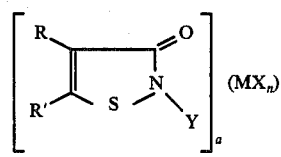 (II)

wherein
Y, R, and R' are as defined above,
M is a cation of a metal, such as barium, cadmium, calcium, chromium, cobalt, copper, iron, lead, lithium, magnesium, manganese, mercury, nickel, sodium, silver, strontium, tin, zinc, or the like;
X is an anion forming a compound with the cation M, wherein the compound has sufficient solubility to form a metal salt complex;
$a$ is the integer 1 or 2; and
$n$ is an integer which for the anion X satisfies the valence of the cation M.

As used in the specification and claims, the term alkyl group is intended to include unsubstituted alkyl groups as well as substituted alkyl groups in which one or more of the hydrogen atoms are replaced by another substituent group. Examples of the substituted alkyl groups which characterize the 3-isothiazolones and the metal salt complexes of the invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, isothiazolonylalkyl, haloalkoxyalkyl, carbamoxyalkyl, azacycloalkylalkyl, such as morpholinoalkyl, piperidinoalkyl, and pyrrolidonylalkyl, and the like. The terms alkenyl group and alkynyl group are intended to include unsubstituted alkenyl and alkynyl groups as well as substituted groups such as haloalkenyl, haloalkynyl, and the like.

The term aralkyl group is intended to include unsubstituted aralkyl groups, e.g. benzyl or phenethyl, as well as substituted aralkyl groups having one or more of the hydrogen atoms on either the aryl ring or the alkyl chain replaced by another substituent group. Examples of the substituted aralkyl groups which characterize the 3-isothiazolones and the metal salt complexes of the invention include halogen-, nitro-, ($C_1$-$C_4$)alkyl-, or ($C_1$-$C_4$)alkoxy-substituted aralkyl groups, and the like.

The term aryl group is intended to include unsubstituted aryl groups, such as phenyl, naphthyl, or pyridyl, as well as such aryl groups having one or more of the hydrogen atoms on the aryl ring replaced by another substituent group. Examples of such substitutent groups include halogen, cyano, nitro, ($C_1$-$C_4$)alkyl, ($C_1$-$C_4$)alkoxy, ($C_1$-$C_4$)alkylacylamino, ($C_1$-$C_4$)carbalkoxy, sulfamyl, and the like.

Representative Y substitutents include hydrogen, methyl, ethyl, propyl, isopropyl, butyl, hexyl, octyl, decyl, pentadecyl, octadecyl, cyclopropyl, cyclohexyl, benzyl, 3,4-dichlorbenzyl, 4-methoxybenzyl, 4-chlorobenzyl, 3,4-dichlorophenyl, 4-methoxyphenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, hydroxybutyl allyl, propynyl, vinyl, carboxyethyl, 1-isothiazolonylethyl, 1,2,2-trichlorovinyl, and the like. Representative R and R' substituents include hydrogen, bromine, chlorine, iodine, methyl, ethyl, propyl, isopropyl, butyl, t-butyl, and the like. The alkyl substituents represented by Y, R, and R' can have either branched- or straight-chain spatial configuration.

Among the anions which X can represent are chloride, bromide, iodide, sulfate, nitrate nitrite, acetate, chlorate, perchlorate, bisulfate, bicarbonate, oxalate, maleate, p-toluenesulfonate, carbonate, phosphate, and the like. The preferred metals from which M is derived are calcium, copper, magnesium, manganese, nickel, and zinc. Among the metal cations embraced by M are cationic complexes of the metal ions, including complexes with ammonia, simple organic amines, and various heterocyclic organic amines such as pyridines, pyrimidines, and the like.

A wide variety of metal nitrates and the metal nitrites can be used to stabilize solutions of isothiazolones and generally any metal nitrate or nitrite which has appreciable solubility in the solution will exert a stabilizing effect. Among the useful metal nitrates are sodium nitrate, potassium nitrate, calcium nitrate, magnesium nitrate, copper nitrate, ferric nitrate, ferrous nitrate, nickel nitrate, zinc nitrate, barium nitrate, manganese nitrate, silver nitrate, cobalt nitrate, and the like. Among the useful metal nitrites are sodium nitrite, potassium nitrite, calcium nitrite, magnesium nitrite, and the like. In a preferred embodiment of the invention, a metal nitrate is used to stabilize the isothiazolone solution. Surprisingly, other common metal salts, including carbonates, sulfates, chlorates, perchlorates, and chlorides are ineffective in stabilizing isothiazolones solutions.

Generally, the metal nitrate or nitrite is used to stabilize the isothiazolone solution in an amount of about 1 to about 30%, preferably about 15 to about 25%, by weight based on the weight of the solution. For example, in a 25% by weight solution of an isothiazolone, about 10 to about 30% by weight of the metal nitrate or nitrite will generally be sufficient to stabilize the solution against chemical decomposition. Of course, the amount of metal nitrate or nitrite needed to stabilize the solution will be partly dependent on the solvent, the isothiazolone and its concentration, the nitrate or nitrite used, the length of time the solution is to be kept, and other related factors.

In a preferred embodiment of the invention, the metal nitrates and metal nitrites are used to stabilize solutions of 3-isothiazolones in water and in polar organic solvents, including alcohols such as methanol, ethanol, propanol, butanol, ethylene glycol, propylene glycol, dipropylene glycol, polypropylene glycol, polyethylene glycol, 2-methoxyyethanol, and the like. Among the applications in which solution of isothiazolones are used are as water-cooling system microbicides, as preservatives for aqueous dispersions of organic polymers, as wood pulp white water slimicides, as cosmetic preservatives, as cutting oil, jet fuel, and heating oil preservatives, and the like. Solutions of isothiazolones are also often used applying an isothiazolone to a solid substrate, such as fabric, leather, or wood, as a preservative, especially in automated treating processes.

The preparation and properties of representative 3-isothiazolones which in solution are stabilized by the metal nitrates and nitrites are described in United States patent applications Ser. No. 836,660, filed on June 25, 1969, by Sheldon N. Lewis et al., Ser. No. 855,046, filed on Sept. 3, 1969, by Sheldon N. Lewis et al., and Ser. No. 142,775, filed on May 12, 1971, by George A. Miller et al., and in U.S. Pat. Nos. 3,517,022 of George A. Miller et al., granted June 23, 1970 and 3,544,480, of Sheldon N. Lewis et al., granted Dec. 1, 1970. When solutions of metal salt complexes of the isothiazolones are to be used, it may be advantageous to prepare the complexes in situ by neutralization of a salt, such as the hydrochloride salt, of the appropriate isothiazolone with a basic metal compound, such as an oxide or carbonate. Optionally, up to about one half mole equivalent of a metal nitrate is added to these solutions, prior to the addition of the metal nitrate stabilizer.

The following examples will further illustrate this invention, but are not intended to limit it in any way. All parts and percentages are by weight and all temperatures in Centigrade, unless otherwise stated. Percentages of the metal nitrates and metal nitrites are based on the molecular weight of the common commercial form.

EXAMPLE 1

This example shows the effect of various metal nitrates in stabilizing aqueous solutions of 3-isothiazolone metal salt complexes. The metal salt complex used in making the aqueous solutions of this representative example is a 3:1 weight ratio of the calcium chloride complexes of 5-chloro-2-methyl-3-isothiazolone and 2-methyl-3-isothiazolone. Aqueous solutions containing 25% by weight of the metal salt complex and from 1.4 to 28.7% by weight of the metal nitrate based on the molecular weight of the common commercial form are prepared and stored for up to 84 days at 50° C. From time to time the solutions are visually examined, and rated as "passed" if they remain clear and contain no or minor traces of yellow precipitate. When the solutions become brown in color or contain significant amounts of brown or black precipitates they are rated "failed". Table I summarizes the results of these tests.

TABLE I

STABILIZED AQUEOUS SOLUTIONS OF 3-ISOTHIAZOLONE METAL SALT COMPLEX
(25% by weight, 50° C)

| Metal Nitrate | Weight % | Appearance (days) | |
|---|---|---|---|
| | | Failed | Passed |
| none | | 10 | |
| $Ca(NO_3)_2 \cdot 4H_2O$ | 28.7 | | 84 |
| $Ca(NO_3)_2 \cdot 4H_2O$ | 14.3 | | 84 |
| $NaNO_3$ | 20.0 | | 63 |
| $Cu(NO_3)_2 \cdot 3H_2O$ | 28.7 | | 84 |
| $Cu(NO_3)_2 \cdot 3H_2O$ | 14.3 | | 84 |
| $Cu(NO_3)_2 \cdot 3H_2O$ | 1.4 | | 25 |
| $Fe(NO_3)_3 \cdot 9H_2O$ | 16.7 | | 25 |
| $Mg(NO_3)_2 \cdot 6H_2O$ | 17.3 | | 84 |
| $Ni(NO_3)_2 \cdot 6H_2O$ | 15.9 | | 84 |
| $Zn(NO_3)_2 \cdot 6H_2O$ | 15.7 | | 84 |

EXAMPLE 2

This example shows the ineffectiveness of metal salts other than metal nitrates and nitrites in stabilizing aqueous solutions of 3-isothiazolones metal salt complexes.

Following the precedure of Example 1 other metal salts were added to aqueous solutions of the same metal salt complex, and rated in a similar way. Table II summarizes the results of these tests.

TABLE II

AQUEOUS SOLUTIONS OF 3-ISOTHIAZOLONE METAL SALT COMPLEX
(25% by weight, 50° C)

| Metal Salt | Weight % | Appearance (days) | |
|---|---|---|---|
| | | Failed | Passed |
| none | | 10 | |
| $CaCO_3$ | 1 | 7 | |
| $CuCl_2 \cdot 2H_2O$ | 12.7 | 10 | |

TABLE II-continued

AQUEOUS SOLUTIONS OF
3-ISOTHIAZOLONE METAL SALT COMPLEX
(25% by weight, 50° C)

| Metal Salt | Weight % | Appearance (days) Failed | Appearance (days) Passed |
|---|---|---|---|
| $CuSO_4 \cdot 5H_2O$ | 15.9 | 10 | |
| $Fe_2(SO_4)_3 \cdot 9H_2O$ | 14.1 | 10 | |
| $FeSO_4 \cdot 7H_2O$ | 18.2 | 10 | |
| $MnSO_4 \cdot H_2O$ | 11.2 | 10 | |
| $Zn(ClO_4O_2 \cdot 6H_2O$ | 14.1 | 10 | |
| $ZnSO_4 \cdot 7H_2O$ | 17.8 | 10 | |
| $CaCl_2$ | 25.0 | 10 | |
| NaCl | 25.0 | 10 | |
| $Ca(ClO_3)_2 \cdot 2H_2O$ | 28.4 | 10 | |
| $Ca(ClO_4)_2$ | 25.0 | 10 | |

EXAMPLE 3

This example shows quantitatively the extent to which chemical decomposition of 3-isothiazolone metal salt complexes in solution is inhibited by metal nitrates and metal nitrites.

Solutions of the metal salt complex used in Example 1 (25% by weight) stabilized with various metal nitrates and nitrites are stored at 50° C for the time indicated and evaluated by gas liquid chromatography (glc) to determine the amount of decomposition of the isothiazolone. Table III summarizes the results of these tests.

TABLE III

% DECOMPOSITION OF METAL SALT COMPLEX IN AQUEOUS SOLUTION

| Metal Nitrate | % Nitrate | Time | % Decomposition |
|---|---|---|---|
| none | — | 10 days | 100 |
| $Ca(NO_3)_2 \cdot 4H_2O$ | 28.7 | 3 months | 10 |
| | | 4.5 months | 20 |
| | | 6 months | 25 |
| | | 9 months | 55 |
| $Ca(NO_3)_2 \cdot 4H_2O$ | 25.0 | 2 months | 0 |
| | | 3 months | 10 |
| | | 6 months | 10 |
| $Ca(NO_3)_2 \cdot 4H_2O$ | 14.3 | 1 month | 10 |
| | | 3 months | 45 |
| | | 4.5 months | 95 |
| $Cu(NO_3)_2 \cdot 3H_2O$ | 25.8 | 3 months | 5 |
| | | 4.5 months | 10 |
| | | 6 months | 10 |
| | | 9 months | 20 |
| $Cu(NO_3)_2 \cdot 3H_2O$ | 25.0 | 3 months | 0 |
| | | 6 months | 0 |
| $Cu(NO_3)_2 \cdot 3H_2O$ | 12.9 | 3 months | 5 |
| | | 4.5 months | 30 |
| | | 6 months | 30 |
| | | 9 months | 40 |
| $Mn(NO_3)_2$ | 25.0 | 6 months | 10 |
| $Mg(NO_3)_2 \cdot 6H_2O$ | 25.0 | 6 months | 10 |
| $Zn(NO_3)_2 \cdot 6H_{months}$ | 5 | | |
| none | | 14 days | 100 |
| $Ca(NO_2)_2 \cdot H_2O$ | 25 | 14 days | 0 |
| $NaNO_2$ | 25 | 14 days | 5 |

The above data demonstrates the effectiveness of metal nitrates and metal nitrites in inhibiting chemical decomposition of aqueous solutions of 3-isothiazolone metal salt complexes.

EXAMPLE 4

This example shows the effect of various metal nitrates in stabilizing aqueous solutions of 3-isothiazolone metal salt complexes prepared in situ.

Solutions (25% by weight) of a 3:1 weight ratio of the hydrochloride salts of 5-chloro-2-methyl-3-isothiazolone and 2-methyl-3-isothiazolone are neutralized with 0.5 or 1.0 mole-equivalent of a metal oxide or metal carbonate. To the solutions is then added 0.5 mole-equivalent of a metal nitrate and up to 25% by weight of additional metal nitrate as a stabilizer. The solutions are stored at 50° C for the time indicated and evaluated by glc to determine the amount of decomposition of the isothiazolone. Table IV summarizes the results of these tests.

TABLE IV

% DECOMPOSITION OF METAL SALT COMPLEXES PREPARED IN SITU
(25% by weight, 50° C)

| Base | Complex Formed Mole-equiv. | Metal Nitrate | Stabilizer Metal Nitrate; | wt. % | Time | % Decomposition |
|---|---|---|---|---|---|---|
| CaO | $CaCl_2$; 1.0 | none | none | | 10 days | 100 |
| CaO | $CaCl_2$; 0.5 | $Ca(NO_3)_2$ | $Ca(NO_3)_2 \cdot 4H_2O$; | 25% | 6 months | 5 |
| $CaCO_3$ | $CaCl_2$; 0.5 | $Zn(NO_3)_2$ | $Zn(NO_3)_2 \cdot 6H_2O$; | 25% | 6 months | 5 |
| $CaCO_3$ | $CaCl_2$; 0.5 | $Mn(NO_3)_2$ | $Mn(NO_3)_2$; | 25% | 6 months | 10 |
| MgO | $MgCl_2$; 0.5 | $Mg(NO_3)_2$ | $Mg(NO_3)_2 \cdot 6H_2O$; | 25% | 3 months | 0 |
| | | | | | 6 months | 10 |
| $MgCO_3$ | $MgCl_2$; 0.5 | $Mg(NO_3)_2$ | $Mg(NO_3)_2 \cdot 6H_2O$; | 12.5% | 3 months | 20 |
| | | | | | 6 months | 35 |
| ZnO | $ZnCl_2$; 0.5 | $Zn(NO_3)_2$ | $Zn(NO_3)_2 \cdot 6H_2O$; | 25% | 6 months | 10 |
| $Na_2CO_3$ | NaCl; 1.0 | $Mg(NO_3)_2$ | $Mg(NO_3)_2 \cdot 6H_2O$; | 25% | 6 months | 35 |
| $Na_2CO_3$ | NaCl; 1.0 | $Mn(NO_3)_2$ | $Mn(NO_3)_2$; | 25% | 6 months | 0 |

EXAMPLE 5

This example shows the effect of various metal salts in stabilizing aqueous solutions of 3-isothiazolones. The 3-isothiazolone used in making the aqueous solutions is a 3:1 weight ratio of 5-chloro-2-methyl-3-isothiazolone and 2-methyl-3-isothiazolone. Aqueous solutions containing 25% by weight of the 3-isothiazolone and 0.5 or 1.0 mole-equivalent of a metal salt are prepared, stored for up to 84 days at 50° C. and rated as in Example 1. Table V summarizes the results of these tests.

TABLE V

AQUEOUS SOLUTIONS OF 5-CHLORO-2-METHYL-
3-ISOTHIAZOLONE/2-METHYL-3-ISOTHIAZOLONE
(25% by weight, 50° C)

| Metal Salt | Mole-equiv. | Appearance (days) Failed | Appearance (days) Passed |
|---|---|---|---|
| none | | 10 | |
| $Ca(NO_3)_2$ | 1.00 | | 84 |
| $Cu(NO_3)_2$ | 1.00 | | 84 |
| $Cu(NO_3)_2$ | 0.50 | | 84 |
| $Mg(NO_3)_2$ | 1.00 | | 84 |
| $Fe(NO_3)_3$ | 1.00 | | 84 |
| $Ni(NO_3)_2$ | 1.00 | | 84 |
| $Zn(NO_3)_2$ | 1.00 | | 84 |
| $CuCl_2$ | 1.00 | 5 | |
| $CuSO_4$ | 1.00 | 5 | |

The above results show the effectiveness of metal nitrates in stabilizing aqueous solutions of 3-isothiazolones and the general ineffectiveness of other metal salts as stabilizers.

EXAMPLE 6

This example shows quantitatively the extent to which chemical decomposition of 3-isothiazolones in solution is inhibited by metal nitrates.

Two aqueous solutions of the 3-isothiazolones (25% by weight) used in Example 5 containing 0.5 and 1.0 mole-equivalent of copper nitrate are evaluated by glc to determine the amount of decomposition of the isothiazolone. Table VI summarizes the results of these tests TABLE VI
AQUEOUS SOLUTIONS OF 5-CHLORO-2-METHYL-3-ISOTHIAZOLONE/2-METHYL-3-ISOTHIAZOLONE
(25% by weight, 50° C)

| Metal Salt | Mole-equiv. | Time | % Decomposition |
|---|---|---|---|
| none | none | 10 days | 70 |
| $Ca(NO_3)_2$ | 1.0 | 3 months | 0 |
| $Cu(NO_2)_2$ | 0.5 | 3 months | 5 |
|  |  | 9 months | 5 |
| $Cu(NO_3)_2$ | 1.0 | 3 months | 0 |
|  |  | 9 months | 5 |

Similarly, aqueous 2-methoxyethanol solutions (20/80) of 2-n-octyl-3-isothiazolone (compound A) and 4-bromo-5-chloro-2-methyl-3-isothiazolone (compound B) stabilized with various metal nitrates are evaluated by glc to determine the amount of decomposition of the isothiazolones. Table VII summarizes the results of these tests.

TABLE VII
AQUEOUS/METHYL CELLOSOLVE SOLUTIONS OF 3-ISOTHIAZOLONES
(1 month, 50° C)

| Compound | Weight % | Metal Nitrate 25% by wt. | % Decomposition |
|---|---|---|---|
| A | 20 | none | 100 |
| A | 20 | $Ca(NO_3)_2 \cdot 4H_2O$ | 5 |
| A | 15 | $Mg(NO_3)_2 \cdot 6H_2O$ | 15 |
| A | 15 | $Zn(NO_3)_2 \cdot 6H_2O$ | 10 |
| B | 23 | none | 100 |
| B | 23 | $Ca(NO_3)_2 \cdot 4H_2O$ | 25 |

EXAMPLE 7

This example shows the effect of various metal nitrates in stabilizing nonaqueous solutions of 3-isothiazolones.

To prepare the solutions, the following procedure is used. A 2.0 g sample of the 3-isothiazolone metal salt complex used in Example 1 (25% by weight), 0.8 g of $Ca(NO_3)_2 \cdot 4H_2O$ (10% by weight), and 5.2 g of dipropylene glycol are placed in a microgrinder apparatus for 10 minutes. The clear, slightly yellow solution which is obtained is stored at 50° C and evaluated as in Example 3. Solutions using methyl cellosolve as a solvent and solutions using magnesium nitrate as a stabilizer are also prepared and evaluated. Table VIII summarizes the results of these tests.

EXAMPLE 8

This example shows the effect of various metal nitrates in stabilizing non-aqueous solutions of 3-isothiazolones. The 3-isothiazolone used in making the non-aqueous solution is an approximate 93:7 weight ratio of 5-chloro-2-methyl-3-isothiazolone and 2-methyl-3-isothiazolone. Nonaqueous solutions containing 25% by weight of the 3-isothiazolone and 1.0 mole-equivalent of the metal nitrates are prepared as described in Example 7, stored for up to 84 days at 50° C, and rated as in Example 1. Table IX summarizes the results of these tests.

TABLE IX
NON-AQUEOUS SOLUTIONS OF 5-CHLORO-2-METHYL-3-ISOTHIAZOLONE/2-METHYL-3-ISOTHIAZOLONE (93:7)
(25% by weight, 50° C)

| Metal Nitrate (1 mole-equiv.) | Solvent | Appearance (days) Failed | Passed |
|---|---|---|---|
| none | dipropylene glycol | 28* |  |
| $Ca(NO_3)_2$ | dipropylene glycol |  | 23 |
| $Zn(NO_3)_2$ | dipropylene glycol |  | 84 |
| none | methanol | 10 | 84 |
| $Ca(NO_3)_2$ | methanol |  | 84 |
| $Zn(NO_3)_2$ | methanol |  | 84 |

*Solution gelled and became cloudy; glc showed 100% decomposition.

The non-aqueous solutions of 3-isothiazolones used in Example 8 containing 1.0 mole-equivalent metal nitrates are evaluated by glc to determine the amount of decomposition of the isothiazolone. Table X summarizes the results of these tests.

TABLE X
NON-AQUEOUS SOLUTIONS OF 5-CHLORO-2-METHYL-3-ISOTHIAZOLONE/2-METHYL-3-ISOTHIAZOLONE (93:7)
(25% by weight, 50° C)

| Metal Nitrate (1 mole-equiv.) | Solvent | Time | % Decomposition |
|---|---|---|---|
| none | dipropylene glycol | 28 days | 100 |
| $Ca(NO_3)_2$ | dipropylene glycol | 3 months | 0 |
| $Zn(NO_3)_2$ | dipropylene glycol | 3 months | 16 |
| $Ca(NO_3)_2$ | methanol | 3 months | 3 |
| $Zn(NO_3)_2$ | methanol | 3 months | 35 |

It is to be understood that changes and variations may be made without departing from the spirit and scope of the invention as defined by the appended claims.

We claim:

1. A method of stabilizing a solution containing a 3-isothiazolone complex of the formula TABLE VIII
NON-AQUEOUS SOLUTIONS OF 5-CHLORO-2-METHYL-3-ISOTHIAZOLONE CALCIUM (II)CHLORIDE/2-METHYL-3-ISOTHIAZOLONE CALCIUM(II) CHLORIDE
(50° C)

| Isothiazolone Wt. % | Metal Nitrate; | wt. % | Solvent | Time | % Decomposition |
|---|---|---|---|---|---|
| 25% | none |  | dipropylene glycol | 1 month | 100 |
| 25% | $Ca(NO_3)_2 \cdot 4H_2O$; | 10% | dipropylene glycol | 2 months | 5 |
| 25% | $Ca(NO_3)_2 \cdot 4H_2O$; | 20% | dipropylene glycol | 3 months | 15 |
|  |  |  |  | 9 months | 35 |
| 25% | $Mg(NO_3)_2 \cdot 6H_2O$; | 10% | dipropylene glycol | 2 months | 5 |
| 25% | $Mg(NO_3)_2 \cdot 6H_2O$; | 20% | dipropylene glycol | 3 months | 5 |
|  |  |  |  | 9 months | 20 |
| 5% | none |  | 2-methoxyethanol | 3 months | 90 |
| 5% | $Ca(NO_3)_2 \cdot 4H_2O$; | 5% | 2-methoxyethanol | 3 months | 10 |
| 10% | none |  | 2-methoxyethanol | 3 months | 95 |
| 10% | $Ca(NO_3)_2 \cdot 4H_2O$; | 10% | 2-methoxyethanol | 3 months | 0 |

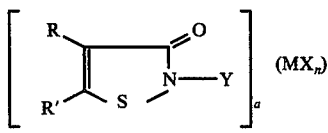

wherein
- Y is a hydrogen atom, an alkyl group of 1 to 18 carbon atoms, an alkenyl or alkynyl group of 2 to 18 carbon atoms, a cycloalkyl group of 3 to 12 carbon atoms, having a 3 to 8 carbon atom ring, an aralkyl group of up to 10 carbon atoms, or an aryl group of up to 10 carbon atoms;
- R is a hydrogen atom, a halogen atom, or a $(C_1-C_4)$alkyl group;
- R' is a hydrogen atom, a halogen atom, or a $(C_1-C_4)$alkyl group;
- M is a cation of barium, cadmium, calcium, chromium, cobalt, copper, iron, lead, magnesium, manganese, mercury, nickel, silver, strontium, tin or zinc;
- X is a chloride, bromide iodide, sulfate, nitrate, nitrite, acetate, chlorate, perchlorate, bisulfate, bicarbonate, oxalate, maleate, p-toluenesulfonate, carbonate, or phosphate anion;
- $a$ is the integer 1 or 2; and
- $n$ is an integer which for the anion X satisfies the valence of the cation M;

against decomposition of the complex, which comprises adding to the solution a stabilizing amount of a metal salt selected from the group consisting of nitrates and nitrites of sodium, potassium, calcium, magnesium, copper, iron, nickel, zinc, barium, manganese, silver, cobalt, and mixtures thereof.

2. The method of claim 1 wherein the solution is an aqueous or polar organic solvent solution.

3. The method of claim 2 wherein the metal salt is added in an amount of about 1 to about 30% by weight of the solution.

4. The method of claim 3 wherein the solution is an aqueous solution.

5. The method of claim 4 wherein
- Y is a hydrogen atom, an unsubstituted alkyl group of 1 to 18 carbon atoms, a $(C_3-C_8)$ cycloalkyl group, an aralkyl group of up to 8 carbon atoms, or a phenyl group.

6. The method of claim 5 wherein
- Y is a hydrogen atom, an unsubstituted $(C_1-C_8)$ alkyl group, a cyclohexyl group, or a benzyl, phenethyl or phenyl group optionally substituted with up to two methyl groups or chlorine atoms.

7. The method of claim 6 wherein the 3-isothiazolone metal salt complex is the calcium chloride complex of 5-chloro-2-methyl-3-isothiazolone or a mixture of the calcium chloride complexes of 5-chloro-2-methyl-3-isothiazolone and 2-methyl-3-isothiazolone.

8. The method of claim 7 wherein the metal salt is calcium nitrate.

9. The method of claim 7 wherein the metal salt is magnesium nitrate.

10. The method of claim 6 wherein the 3-isothiazolone metal salt complex is the magnesium chloride complex of 5-chloro-2-methyl-3-isothiazolone or a mixture of the magnesium chloride complexes of 5-chloro-2-methyl-3-isothiazolone and 2-methyl-3-isothiazolone.

11. The method of claim 10 wherein the metal salt is magnesium nitrate.

12. The method of claim 2 wherein the solution is an alcoholic solution.

13. The method of claim 12 wherein the alcohol is propylene glycol.

14. A stabilized solution which comprises a solvent, a 3-isothiazolone complex of the formula

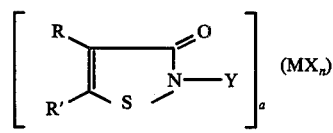

wherein p1 Y is a hydrogen atom, an alkyl group of 1 to 18 carbon atoms, an alkenyl or alkynyl group of 2 to 18 carbon atoms, a cycloalkyl group of 3 to 12 carbon atoms, having a 3 to 8 carbon atoms ring, an aralkyl group of up to 10 carbon atoms, or an aryl group of up to 10 carbon atoms;
- R is a hydrogen atom, a halogen atom, or a $(C_1-C_4)$ alkyl group;
- R' is a hydrogen atom, a halogen atom, or a $(C_1-C_4)$alkyl group;
- M is a cation of barium, cadmium, calcium, chromium, cobalt, copper, iron, lead, magnesium, manganese, mercury, nickel, silver, strontium, tin or zinc;
- X is a chloride, bromide, iodide, sulfate, nitrate, nitrite, acetate, chlorate, perchlorate, bisulfate, bicarbonate, oxalate, maleate, p-toluenesulfonate, carbonate, or phosphate anion;
- $a$ is the integer 1 or 2; and
- $n$ is an integer which for the anion X satisfies the valence of the cation M;

and a metal salt selected from the group consisting of nitrates and nitrites of sodium, potassium, calcium, magnesium, copper, iron, nickel, zinc, barium, manganese, silver, and cobalt, and mixtures thereof.

15. The solution of claim 14 wherein the solvent is water.

16. The solution of claim 15 wherein the metal salt is calcium nitrate or magnesium nitrate.

* * * * *

UNITED STATES PATENT AND TRADEMARK OFFICE
CERTIFICATE OF CORRECTION

PATENT NO. : 4,067,878
DATED : January 10, 1978
INVENTOR(S) : George A. Miller and Ernest D. Weiler It is certified that error appears in the above—identified patent and that said Letters Patent are hereby corrected as shown below:

Column 5, Table II, line 10

$Zn(ClO_4)_2 \cdot 6H_2O$  14.1  10

Column 5, Table III, line 62

$Zn(NO_3)_2 \cdot 6H_2O$  25.0  6 months  5

Column 10, claim 14, line 27 wherein Y is a hydrogen atom....

*Signed and Sealed this*

*Twenty-third* Day of *May 1978*

[SEAL]

Attest:

RUTH C. MASON
*Attesting Officer*

LUTRELLE F. PARKER
*Acting Commissioner of Patents and Trademarks*